(12) United States Patent
Sørensen

(10) Patent No.: US 11,794,389 B2
(45) Date of Patent: Oct. 24, 2023

(54) TIP PART ASSEMBLY FOR AN ENDOSCOPE

(71) Applicant: Ambu A/S, Ballerup (DK)

(72) Inventor: Morten Sørensen, Ballerup (DK)

(73) Assignee: AMBU A/S, Ballerup (DK)

( * ) Notice: Subject to any disclaimer, the term of this patent is extended or adjusted under 35 U.S.C. 154(b) by 86 days.

(21) Appl. No.: 17/013,488

(22) Filed: Sep. 4, 2020

(65) Prior Publication Data

US 2021/0068634 A1 Mar. 11, 2021

(30) Foreign Application Priority Data

Sep. 6, 2019 (EP) .................................... 19195989
Sep. 6, 2019 (EP) .................................... 19195995
(Continued)

(51) Int. Cl.
*A61B 1/05* (2006.01)
*A61B 1/06* (2006.01)
(Continued)

(52) U.S. Cl.
CPC ........ *B29C 45/14467* (2013.01); *A61B 1/009* (2022.02); *A61B 1/0011* (2013.01);
(Continued)

(58) Field of Classification Search
CPC ..... A61B 1/07; A61B 1/00103; A61B 1/0011; A61B 1/05; A61B 1/0669; A61B 1/0684;
(Continued)

(56) References Cited

U.S. PATENT DOCUMENTS

| 4,779,130 A | 10/1988 | Yabe |
| 5,609,561 A | 3/1997 | Uehara et al. |

(Continued)

FOREIGN PATENT DOCUMENTS

| CN | 201499375 U | 6/2010 |
| CN | 104995907 B | 5/2019 |

(Continued)

OTHER PUBLICATIONS

Extended search report in European Application No. 2019 1424, dated Feb. 1, 2021.
(Continued)

*Primary Examiner* — John P Leubecker
(74) *Attorney, Agent, or Firm* — Faegre Drinker Biddle & Reath LLP

(57) ABSTRACT

A method of manufacture of a tip part assembly for an endoscope having a proximal end and a distal end opposite from the proximal end, the method including: providing a bending section having a proximal end and a distal end, providing a camera assembly including a camera module, providing a substantially tubular circumferential wall having a proximal end and a distal end opposite from the proximal end, providing a distal end wall, arranging the camera module to be held by or attached to the distal end wall, manufacturing a housing by adjoining the distal end wall to the distal end of the circumferential wall, the housing including the circumferential wall and the distal end wall and enclosing a spacing that houses at least a portion of the camera module, and adjoining the distal end of the bending section and the proximal end of the housing.

14 Claims, 7 Drawing Sheets

(30) Foreign Application Priority Data

Sep. 6, 2019 (EP) .................................... 19195996
Sep. 6, 2019 (EP) .................................... 19195998

(51) Int. Cl.

| | |
|---|---|
| A61B 1/015 | (2006.01) |
| A61B 1/018 | (2006.01) |
| B29C 45/14 | (2006.01) |
| A61B 1/00 | (2006.01) |
| A61B 1/07 | (2006.01) |
| A61B 1/005 | (2006.01) |
| B29K 105/00 | (2006.01) |
| B29L 31/00 | (2006.01) |
| A61B 1/307 | (2006.01) |

(52) U.S. Cl.
CPC ...... *A61B 1/00094* (2013.01); *A61B 1/00105* (2013.01); *A61B 1/00124* (2013.01); *A61B 1/015* (2013.01); *A61B 1/018* (2013.01); *A61B 1/051* (2013.01); *A61B 1/0684* (2013.01); *A61B 1/07* (2013.01); *A61B 1/307* (2013.01); *B29K 2105/0097* (2013.01); *B29L 2031/7546* (2013.01)

(58) Field of Classification Search
CPC . A61B 1/00009; A61B 1/0002; A61B 1/3137; A61B 1/053; A61B 1/04; A61M 25/0045; G02B 23/2484; G02B 23/2469
USPC .................................................. 600/129, 130
See application file for complete search history.

(56) References Cited

U.S. PATENT DOCUMENTS

| | | | |
|---|---|---|---|
| 5,951,464 A | 9/1999 | Takahashi et al. | |
| 7,662,094 B2 | 2/2010 | Iddan | |
| 7,833,151 B2 | 11/2010 | Khait et al. | |
| 8,414,480 B2 | 4/2013 | Kendale et al. | |
| 8,485,966 B2 | 7/2013 | Robertson | |
| 9,125,582 B2 | 9/2015 | Petersen | |
| 9,158,037 B2 | 10/2015 | Otsuka et al. | |
| 9,622,649 B2 | 4/2017 | Lin | |
| 9,814,371 B2 | 11/2017 | Segi et al. | |
| 9,866,738 B2 | 1/2018 | Kojima | |
| 10,025,088 B2 | 7/2018 | Handte et al. | |
| 2002/0193663 A1* | 12/2002 | Matsuura | A61B 1/051 600/129 |
| 2003/0113642 A1* | 6/2003 | Kami | G03G 5/0217 430/57.2 |
| 2004/0027459 A1 | 2/2004 | Segawa et al. | |
| 2004/0242963 A1* | 12/2004 | Matsumoto | A61B 1/00101 600/176 |
| 2005/0143659 A1 | 6/2005 | Saiga | |
| 2005/0222499 A1* | 10/2005 | Banik | A61B 1/0676 600/156 |
| 2005/0277340 A1* | 12/2005 | Gordon | H01R 13/6599 439/676 |
| 2006/0264704 A1 | 11/2006 | Fujimori et al. | |
| 2007/0027360 A1* | 2/2007 | Mitsuya | A61B 1/00071 600/141 |
| 2007/0249907 A1* | 10/2007 | Boulais | A61B 5/064 600/179 |
| 2008/0132760 A1 | 6/2008 | Takeuchi | |
| 2008/0242935 A1* | 10/2008 | Inoue | A61B 1/07 600/176 |
| 2008/0266441 A1* | 10/2008 | Ichimura | H04N 5/2254 348/340 |
| 2008/0312504 A1 | 12/2008 | Kimoto | |
| 2009/0012358 A1 | 1/2009 | Ichihashi et al. | |
| 2009/0259101 A1 | 10/2009 | Unsai | |
| 2009/0260553 A1 | 10/2009 | Skovbo | |
| 2009/0295913 A1 | 12/2009 | Sato et al. | |
| 2010/0016667 A1 | 1/2010 | Segawa et al. | |
| 2010/0185052 A1 | 7/2010 | Chang | |
| 2011/0118549 A1 | 5/2011 | Han | |
| 2011/0288372 A1 | 11/2011 | Petersen | |
| 2012/0197081 A1* | 8/2012 | Kimura | A61B 1/051 600/110 |
| 2012/0220825 A1 | 8/2012 | Kimura | |
| 2012/0229615 A1 | 9/2012 | Kirma et al. | |
| 2013/0041223 A1 | 2/2013 | Kato | |
| 2013/0060083 A1 | 3/2013 | Oku | |
| 2013/0150667 A1* | 6/2013 | Mitamura | A61B 1/00117 600/104 |
| 2013/0172678 A1* | 7/2013 | Kennedy, II | A61B 1/051 600/109 |
| 2013/0175720 A1 | 7/2013 | Otsuka et al. | |
| 2013/0271588 A1 | 10/2013 | Kirma et al. | |
| 2014/0073853 A1 | 3/2014 | Swisher et al. | |
| 2014/0100421 A1* | 4/2014 | Dejima | A61B 1/0669 600/101 |
| 2014/0142384 A1* | 5/2014 | Chung | A61B 1/005 600/117 |
| 2014/0210976 A1 | 7/2014 | Lin | |
| 2014/0330081 A1* | 11/2014 | Imai | A61B 1/0008 600/129 |
| 2015/0005580 A1 | 1/2015 | Petersen | |
| 2015/0062316 A1 | 3/2015 | Haraguchi et al. | |
| 2015/0094534 A1 | 4/2015 | Yamada | |
| 2015/0148603 A1 | 5/2015 | Holste | |
| 2015/0312457 A1 | 10/2015 | Kojima | |
| 2015/0358518 A1 | 12/2015 | Ishii et al. | |
| 2015/0378144 A1 | 12/2015 | Handte et al. | |
| 2016/0029879 A1 | 2/2016 | Ishikawa | |
| 2016/0051222 A1 | 2/2016 | Imahashi | |
| 2016/0209637 A1 | 7/2016 | Fujimori | |
| 2016/0235629 A1 | 8/2016 | Allyn et al. | |
| 2016/0287060 A1 | 10/2016 | Usuda et al. | |
| 2016/0313552 A1 | 10/2016 | Tomatsu | |
| 2017/0035279 A1 | 2/2017 | Fujii | |
| 2017/0108691 A1 | 4/2017 | Kitano | |
| 2017/0108692 A1 | 4/2017 | Kitano et al. | |
| 2017/0123200 A1 | 5/2017 | Suyama | |
| 2017/0245734 A1* | 8/2017 | Kaneko | A61B 1/307 |
| 2017/0251914 A1 | 9/2017 | Kitano | |
| 2017/0325663 A1 | 11/2017 | Levy et al. | |
| 2018/0070803 A1 | 3/2018 | Mikami | |
| 2018/0153381 A1 | 6/2018 | Wei et al. | |
| 2018/0160893 A1* | 6/2018 | Truckai | A61B 1/00071 |
| 2018/0168041 A1 | 6/2018 | Govrin et al. | |
| 2018/0242822 A1 | 8/2018 | Hamazaki | |
| 2018/0317756 A1 | 11/2018 | Unsai | |
| 2019/0150711 A1 | 5/2019 | Chiu et al. | |
| 2019/0191968 A1 | 6/2019 | Tsumaru | |
| 2019/0282070 A1* | 9/2019 | Vilhelmsen | A61B 1/00096 |
| 2020/0163535 A1 | 5/2020 | Sekido | |
| 2020/0178766 A1 | 6/2020 | Hirokazu | |
| 2020/0192078 A1 | 6/2020 | Spring et al. | |
| 2020/0225461 A1 | 7/2020 | Aizenfeld et al. | |
| 2020/0288953 A1 | 9/2020 | Sørensen et al. | |
| 2020/0297193 A1* | 9/2020 | Takahashi | G02B 7/021 |
| 2021/0068640 A1 | 3/2021 | Sørensen | |
| 2021/0068641 A1 | 3/2021 | Sørensen | |
| 2021/0068642 A1 | 3/2021 | Sørensen | |
| 2021/0105386 A1 | 4/2021 | Satake | |
| 2021/0153729 A1* | 5/2021 | Kirma | H04N 5/2258 |
| 2022/0061630 A1* | 3/2022 | Yan | H05K 1/189 |

FOREIGN PATENT DOCUMENTS

| | | |
|---|---|---|
| DE | 102010034623 A1 | 2/2012 |
| EP | 0306723 B1 | 3/1993 |
| EP | 0754429 B1 | 9/2004 |
| EP | 2110069 B1 | 3/2011 |
| EP | 2594307 A1 | 5/2013 |
| EP | 2692227 A1 | 2/2014 |
| EP | 2692277 A1 | 2/2014 |
| EP | 2913850 A1 | 9/2015 |
| EP | 2594307 B1 | 9/2016 |
| EP | 2692227 B1 | 8/2018 |

(56) References Cited

FOREIGN PATENT DOCUMENTS

| | | | |
|---|---|---|---|
| EP | 2677736 B1 | | 11/2018 |
| JP | 2004008638 A | | 1/2004 |
| JP | 2008118568 A | | 5/2008 |
| JP | 2010005277 A | | 1/2010 |
| JP | 2011200397 A | * | 10/2011 |
| JP | 2011200397 A | | 10/2011 |
| JP | 2011200399 A | | 10/2011 |
| JP | 2011217887 A | | 11/2011 |
| JP | 2012201065 A | * | 10/2012 |
| JP | 2015002805 A | | 1/2015 |
| JP | 2015058118 A | | 3/2015 |
| JP | 5977892 B1 | | 8/2016 |
| JP | 2016221316 A | | 12/2016 |
| JP | 2017074207 A | | 4/2017 |
| JP | 2018-093907 A | | 6/2018 |
| WO | 01/10295 A1 | | 2/2001 |
| WO | 2008/023965 A1 | | 2/2008 |
| WO | 2010066790 A1 | | 6/2010 |
| WO | 2014203604 A1 | | 12/2014 |
| WO | 2018/022402 A1 | | 2/2018 |
| WO | 2018/022418 A2 | | 2/2018 |
| WO | 2019138462 A1 | | 7/2019 |

OTHER PUBLICATIONS

Extended search report in European Application No. 1919 5995, dated Dec. 13, 2019.
Extended search report in European Application No. 1919 5996, dated Dec. 13, 2019.
Extended search report in European Application No. 1919 5998, dated Dec. 2, 2019.
Search Report issued by the European Patent Office, dated Jan. 3, 2020, for Application No. EP19195989, 9 pages.
Examination Report issued in EP 19 195 998.0, dated Jun. 28, 2023, 5 pages.
Examination Report issued in EP 20 191 424.9, dated Jul. 5, 2023, 5 pages.

* cited by examiner

Section A-A

TIP PART ASSEMBLY FOR AN ENDOSCOPE

CROSS-REFERENCE TO RELATED APPLICATIONS

The present application claims priority from, and the benefit of, European Patent Application Nos. 19195989.9, 19195995.6, 19195996.4, and 19195998.0, filed Sep. 6, 2019, which applications are incorporated by reference herein in their entirety.

Commonly owned U.S. patent application Ser. Nos. 17/013,519, 17/013,445, and 17/013,463, filed concurrently with the present application, claim priority from European Patent Application Nos. 19195989.9, 19195995.6, 19195996.4, and 19195998.0, and are incorporated by reference herein in their entirety.

TECHNICAL FIELD

The present disclosure relates to endoscopes and more specifically to a tip part assembly for an endoscope.

BACKGROUND

Endoscopes are well known for visually inspecting difficult to access places such as human body cavities. Typically, the endoscope comprises an elongated insertion tube with a handle at the proximal end, as seen from the operator, and visual inspection means, such as a built-in camera, at the distal end of the elongated insertion tube. This definition of the terms distal and proximal, i.e. proximal being the end closest to the operator and distal being the end remote from the operator, as used herein for endoscopes in general, is adhered to in the present specification.

As the name indicates, endoscopes are used for seeing inside things, such as lungs or other human body cavities of a patient. Modern endoscopes are therefore typically equipped with a light source and a vision receptor including a vision sensor, such as a camera or an image sensor. Provided that sufficient light is present, it is possible for the operator to see where the endoscope is steered and to set the target of interest once the tip has been advanced thereto. This therefore normally requires illumination of the area in front of the distal tip of the endoscope, in particular the field of vision of the camera(s). The light source, such as a light emitting diode, LED, or an optical fibre, may provide illumination.

Electrical wiring for the camera and other electronics, such as LED lighting accommodated in the tip part assembly at the distal end, run along the inside of the elongated insertion tube from the handle to the tip part assembly. Instead of using cameras, endoscopes may also be fibre-optic, in which case the optical fibres run along the inside of the elongated insertion tube to the tip part assembly. For some applications, a working or suction channel may run along the inside of the insertion tube from the handle to the tip part assembly, e.g. allowing liquid to be removed from the body cavity or allowing for insertion of surgical instruments or the like, into the body cavity. The suction channel may be connected to a suction connector, typically positioned at a handle at the proximal end of the insertion tube. For other applications, the working or suction channel may be omitted.

In order to be able to manoeuvre the endoscope inside the body cavity, the distal end of the endoscope may comprise a bending section with increased flexibility, e.g. an articulated tip part assembly allowing the operator to bend this section. Typically, this is done by tensioning or slacking steering wires also running along the inside of the elongated insertion tube from the articulated tip part assembly to a control mechanism of the handle.

Some prior art tip part assemblies include a housing, in a spacing of which a camera assembly is positioned. Such housings are manufactured, typically molded, in one or more pieces and typically include an outer or external surface for facing the environment, although part of this outer surface may be covered by a flexible sleeve. If the housing is in more pieces, the pieces are typically assembled before components of the tip parts assembly, such as a camera module, are positioned within the housing.

For some types of endoscopes, such as uretheroscope, there is a desire to provide the tip part assembly of the endoscope with a smaller diameter or cross sectional extent, especially where the tip part assembly is to be inserted into narrower body cavities. In very narrow body cavities, even a reduction of 1 mm or less in the cross-sectional extent of a tip part assembly can have a noticeable effect on the comfort of the patient and may even make it possible to reach body areas not otherwise accessible. Providing a small size of the tip part assembly can especially be a challenge in cases where the endoscope comprises both a camera and a working channel extending through the tip part assembly since the camera and working channel are positioned one above the other within the tip part assembly, which takes up space in a radial direction of the tip part assembly.

A general desire in the field of endoscopy is to electrically insulate the insertion tube, and thus especially the tip part assembly, from the outside, so as to mitigate the risk of an insulation breakdown and a resulting excessive leakage current.

A desire of the methods and the tip part assemblies according to this disclosure may be to provide and easy assembly and/or reduce the cost of assembly of a tip part assembly and/or to allow for use of a broader range of materials and/or to enable use of less materials in parts of a tip part assembly.

It is therefore desirable to provide a tip part assembly with smaller dimensions for an endoscope, such as an uretheroscope, having electrically insulating properties and being structurally stable.

SUMMARY

On this background, an object of the methods and the tip part assemblies may be to mitigate one or more of these desires.

A first embodiment of a first aspect of this disclosure relates to a method of manufacture of a tip part assembly for an endoscope, the tip part assembly having a proximal end for being connected to other parts of the endoscope and a distal end positioned oppositely from the proximal end, the method comprising the steps of: a) providing a bendable bending section, the bending section including a proximal end and a distal end, b) providing a camera assembly comprising a camera module, c) providing a substantially tubular circumferential wall, the circumferential wall comprising a proximal end and a distal end, the circumferential wall proximal end being positioned oppositely from the circumferential wall distal end, d) providing a distal end wall, e) arranging the camera module so that the camera module is held by or attached to the distal end wall, f) subsequent to step e), manufacturing a housing of the tip part assembly by adjoining the distal end wall to the distal end of the circumferential wall so that the housing comprises the circumferential wall and the distal end wall, and so that the circumferential wall and the distal end wall enclose a spacing, at least a portion of the camera module being housed in the spacing, and g) subsequent to step f), adjoining the distal end of the bending section and the proximal end of the housing, so that the tip part assembly comprises the bending section, the camera assembly, and the housing, the camera assembly being at least partly housed in the spacing, the distal end wall being positioned at the distal end of the tip part assembly.

A second aspect relates to a method of manufacture of a tip part assembly for an endoscope, the tip part assembly having a proximal end for being connected to other parts of the endoscope and a distal end positioned oppositely from the proximal end, the method comprising the steps of: a) providing a bendable bending section, the bending section including a proximal end and a distal end, b) providing a camera assembly comprising a camera module, c) extruding a substantially tubular circumferential wall, the circumferential wall comprising a proximal end and a distal end, the circumferential wall proximal end being positioned oppositely from the circumferential wall distal end, d) providing a distal end wall, e) arranging the camera module so that the camera module is held by or attached to the distal end wall, f) manufacturing a housing of the tip part assembly by adjoining the distal end wall to the distal end of the circumferential wall so that the housing comprises the circumferential wall and the distal end wall, and so that the circumferential wall and the distal end wall enclose a spacing, and g) adjoining the distal end of the bending section and the proximal end of the housing, so that the tip part assembly comprises the bending section, the camera assembly, and the housing, the camera assembly being at least partly housed in the spacing, the distal end wall being positioned at the distal end of the tip part assembly.

The methods according to this disclosure may include that attachment of the camera module to the distal end wall occurs before the circumferential wall is adjoined with the distal end wall. This may make it easier, e.g. for an assembler, to attach the camera module since more space may be available when the circumferential wall is not yet provided to enclose the camera module. This may again ensure that the camera module is correctly positioned with respect to the other parts of the tip part assembly. The methods according to this disclosure may include that the camera assembly further comprises a circuit board in electrical connection with the camera module.

The methods according to this disclosure may also provide more freedom of choice of method of manufacture of the circumferential wall. For example, it may be possible to manufacture the circumferential in an extrusion process. Extrusion processes typically have the advantage, e.g. compared to molding processes, that a very well-defined cross-sectional profile of the extruded object can be obtained. Since tolerances are then smaller, extruding the circumferential wall may entail that the circumferential wall can be made with a thin wall thickness without compromising insulation and structural stability of the housing. This means that the overall cross-sectional dimensions of the tip part assembly can also be made smaller. Furthermore, circumferential wall material may be saved, and electrical insulation of the circumferential wall and the housing may be more secure. Extruded objects are often also more structurally stable so that increased structural stability of the circumferential wall and/or housing and/or tip part assembly can potentially be achieved.

Compared to solutions where a light guide is molded in one piece with a circumferential wall or a housing, the methods according to this disclosure may also make it possible to increase a length and flexibility of the circumferential wall, which can allow for the circumferential wall to form part of or cover at least part of the bending section of the tip part assembly.

Compared to solutions where a light guide is molded in one piece with a circumferential wall or a housing, the methods according to this disclosure may also make it possible to increase size or dimensions of the light guide and/or provide more freedom regarding positioning thereof, see further below.

Step d) of the methods according to this disclosure may alternatively or additionally include extruding a tubular or substantially tubular circumferential wall part, wherein at least a part of the circumferential wall part forms the circumferential wall of the housing. For example, a long circumferential wall part may be extruded, and one or more circumferential walls may be cut from the long circumferential wall part.

The term "endoscope" may be defined as a device suitable for examination of natural and/or artificial body openings, e.g. for exploration of a lung cavity. Additionally, or alternatively, the term "endoscope" may be defined as a medical device.

The embodiments of this disclosure may comprise the bending section may comprise a number of hingedly interconnected segments including the distal end segment, a proximal end segment, and a plurality of intermediate segments positioned between the proximal end segment and the distal end segment. At least one hinge member may interconnect adjacent segments with each other. The bending section may be a section allowing the tip part assembly to bend relative to an insertion tube, potentially so as to allow an operator to manipulate the tip part assembly while inserted into a body cavity of a patient. The bending section may be molded in one piece or may be constituted by a plurality of molded pieces.

The bending section may or may not be attached to the housing by introducing a holder ring therebetween as is known in the art. An adhesive may be separately applied to attach the bending section end segment to the housing or, if a holder ring is present, to attach the distal end segment and the housing to the holder ring.

The circumferential wall may be an outer or exterior wall and may include an outer surface of the tip part assembly for facing the environment. Potentially, no parts of or only a sleeve of the tip part assembly are positioned outside an outer circumference of the circumferential wall.

Manufacture of the circumferential wall may include extrusion of the circumferential wall or a circumferential wall part through a die, the die potentially having a ring-shaped cross section.

The circumferential wall may have a length in a longitudinal direction in the range of 3-15, such as 5-10 mm. This longitudinal direction may extend along a centre axis of the circumferential wall and/or may extend from the proximal towards the distal end of the tip part assembly.

The circumferential wall may extend to at least partly cover or enclose the bending section and/or a bending section distal end segment. The circumferential wall may extend to at least partly cover or enclose the bending section or a bending section distal end segment. The circumferential wall may be flexible and/or bendable, potentially allowing the circumferential wall to follow bending of the bending section, especially if the circumferential wall is positioned to cover at least part of the bending section.

The circumferential wall may define an outer surface of the tip part assembly, potentially at least partly covered by a sleeve, the sleeve potentially extending along at least part of an outer surface of the bending section and the circumferential wall.

A wall thickness of the circumferential wall may be less than 0.25, 0.2, 0.15, 0.14, or 0.13 mm. This may be achieved by extruding the circumferential wall.

The circumferential wall may be provided separately from or non-integral with the distal end wall before they are adjoined.

In step e) of the methods of this disclosure, the circumferential wall may be positioned away from or at a distance from the distal end wall or so that the circumferential wall does not enclose the camera module, the camera assembly, or any other components of the tip part assembly, which may allow for more space around the camera module and distal end wall during step e).

The circumferential wall may comprise or consist or substantially consist of: ABS (Acrylonitrile-Butadine-Styrene), Acrylic, EVA (Ethylene-Vinyl-Acetate), Flexible PVC (Poly Vinyl Chloride), HDPE (High Density Polyethylene), LDPE (Low Density Polyethylene), PC (Polycarbonate), PP (Polypropylene), PU (Polyurethane), Rigid PVC (Poly Vinyl Chloride), TPE (Thermoplastic elastomers) or combinations thereof. The distal end wall may comprise or consist or substantially consist of the same material as listed for the circumferential wall.

Adjoining may be performed by means of an adhesive, which may be applied to the distal end of the bending section and/or to the proximal end of the housing. The adhesive used to adjoin the distal end of the bending section and the proximal end of the housing may be the same types of adhesive as the one used to adjoin the distal end wall and the circumferential wall.

The housing and/or circumferential wall and/or distal end wall may be of or comprise an electrically insulating and/or a transparent material. The housing and/or circumferential wall and/or distal end wall may be of or comprise plastic materials, polymers or plastic polymers. The transparent material may comprise or consist or substantially consist of a transparent plastic or plastic polymer material, such as: a polycarbonate (PC) polymethylmethacrylate (PMMA), Polyethylene Terephthalate (PET), Amorphous Copolyester (PETG), Polyvinyl Chloride (PVC), Liquid Silicone Rubber (LSR), Polyethylene (PE), Fluorinated Ethylene Propylene (FEP), Styrene Methyl Methacrylate (SMMA), Styrene Acrylonitrile Resin (SAN) and/or Methyl Methacrylate Acrylonitrile Butadiene Styrene (MABS) or combinations thereof. Alternatively or additionally, they made be of or comprise a metal.

The distal end wall and the circumferential wall may be of or may comprise different materials.

The distal end wall may be positioned at the distal end of the assembled tip part assembly. The distal end wall may comprise a holding section for holding the camera module, the camera module in step e) being attached to and/or held in the holding section. The holding section may include an opening or hole in the distal end wall, which opening may be rectangular and/or may be shaped to correspond to an outer surface of the camera module at the distal end of the camera module. The camera module distal end may be arranged in the opening in step e), potentially by sliding the camera module distal end into the opening, potentially from a rear or proximal end of the opening and/or potentially in a longitudinal, distal direction. Alternatively, a distal front surface of the camera module may be provided proximally of the distal end wall, potentially adjacent to or abutting a distal end wall proximal surface, whereby the distal end wall may not include a camera module opening, but rather extends in front of the camera module distal end surface. In this case, the distal end wall may be transparent to allow light to shine through the distal end wall into the camera module.

A holding bracket may extend from a distal end wall proximal surface to enclose at least part of the camera module, and may potentially extend along one or more side surfaces of the came module. A backstop may be provided e.g. on inner surfaces of the opening. Such a backstop may stop the camera module distal end from being slid through the opening and/or may allow for the camera module to be properly positioned at a desired location with respect to the distal end wall when being slid into the opening. In a final position of the camera module, a camera module front surface, which may be a distal lens front surface, may be positioned at a distance from a distal end wall distal or outer surface or may be plane with a distal end wall distal surface. An adhesive may be applied or injected into a slot between the camera module distal end and the opening. This adhesive may be applied together with an adhesive applied within the spacing.

The camera assembly may be a sub-assembly of the tip part and may comprise a camera housing, in which the camera module with the image sensor and lens stack may be arranged. Outer surfaces of the camera module or a camera module housing of the camera module may be substantially box-shaped and/or parallelepipedal. The camera housing may house at least a part of the lens stack and/or a part of the image sensor.

The lens stack may be positioned distally of or in front of the image sensor, may include two or more lenses and may include a proximal lens and a distal lens. The camera module may further comprise a lens barrel which may hold and encase the lens stack. The lens stack may be stacked and/or the lens barrel may extend in the longitudinal direction. A connection surface may be positioned proximally of or behind the image sensor. The connection surface may face in a proximal direction. The lens stack or the lens barrel may have a longitudinally extending centre line, which may be, or may be coinciding with, a centre line of the camera module.

The at least one lens, potentially the plurality of lenses, may be of one or more types chosen from the group consisting of: concave, convex, plano-concave, plano-convex, bi-convex, bi-concave.

The circumferential wall may be cylindrical or circular cylindrical or substantially cylindrical or circular cylindrical.

The circumferential wall may have a fixed or constant cross-sectional profile. This profile may be circular or substantially circular, but other profiles are also possible, e.g. ellipsoid.

The circumferential wall may be tubular and/or pipe-shaped and/or tube-shaped and/or ring-shaped or a ring.

The distal end wall may be provided in step d) as a part separate from the circumferential wall, or the distal end wall and the circumferential wall may in step d) be provided as two separate pieces or not in one piece.

The distal end wall may be molded.

The electrical connection between the circuit board and the camera module may be established in step b) and/or before, during or after any one of steps e), f), and g).

The circuit board may be a printed circuit board (PCB) or a flexible printed circuit (FPC). The housing may be attached to the circuit board by means of the hardened adhesive. The entire or substantially the entire circuit board may be embedded in the adhesive. The circuit board may be in electrical connection with the camera module by a connection surface thereof.

FPCs may, throughout this specification, be a single- or double-sided flexible circuit or a rigid-flex circuit, and may comprise one or more layers of conductive material and two or more layers of insulating material, and/or may be a flexible flat cable having one or more conductors. In some embodiments, the FPC may be connected to a second flexible printed circuit and/or to a printed circuit board (PCB). A PCB may comprise one or more cupper layers and one or more layers of insulating materials, such as layers of a FR-4 (flame retardant) composite material.

The tip part assembly may comprise the bending section and a tip part, the tip part comprising at least the camera assembly and the housing.

An adhesive may be filled into the spacing of the housing through an open proximal end of the housing so that the camera assembly is at least partly embedded in the adhesive.

The adhesive may be allowed or caused to harden, whereby the adhesive attaches the housing and the camera assembly to each other.

The adhesive may be a liquid adhesive which may be of low dynamic viscosity, such as a dynamic viscosity below or equal to 200, 150, 120, 110 or 100 cP (centipoise, which is equal to mPa*s). This may ensure that the adhesive reaches all corners or substantially all corners of a free volume of the spacing.

The adhesive may be poured into the spacing. The adhesive may be injected into the spacing. The adhesive may be poured into the spacing through an open proximal end of the housing. The adhesive may be injected into the spacing through an injection needle or a nozzle inserted through or positioned above an open proximal end of the housing.

A predefined amount of adhesive corresponding to a desired amount of adhesive in the spacing may be measured off during filling. Alternatively, or additionally, an upper or top level of the adhesive may be measured during filling to ensure a predefined amount of adhesive is filled into the housing.

The adhesive may be or may function as a potting material and may be unhardened or uncured when filling out the spacing. The adhesive may be cured after being filled into the spacing.

The adhesive may have electrically insulating properties and/or may be a potting material, e.g. such as disclosed in JP2011200399.

The adhesive and/or potting material may comprise or consist of or substantially consist of polyurethane adhesives, silicone adhesives, UV adhesives, thermosetting plastics, silicone rubber gels, epoxy resins, polyurethane, silicone or combinations thereof.

The adhesive and/or potting material may be heat cured, chemically cured, radiation cured (such as UV light cured) or moisture cured etc.

An electronic cable or electronic wires for connecting the circuit board to other parts of the endoscope may be at least partly embedded in the adhesive.

The tip part assembly may further include at least one light-emitting diode or LED for illuminating a target of the endoscope. The at least one light-emitting diode or LED may be positioned in the spacing before filling adhesive into the spacing. The LED(s) may be embedded or substantially embedded in the adhesive. The circuit board may include an arm leading to and connected to the at least one LED.

The term "target" or "target area" in the context of this specification, may be understood as an area of interest that the tip part assembly of the endoscope is being used to analyze.

The tip part assembly may also include one or more light guides and/or LED lenses for guiding light from respective LED(s) to e.g. a front or distal end surface or distal end wall of the tip part assembly and/or a housing thereof. The light guide(s) may extend from the distal end of the tip part assembly to a respective LED or a respective set of LEDs. In some embodiments, the light guides are made from a transparent material. The light guide(s) may be molded and/or may comprise a portion abutting the camera assembly and/or be arranged in front of the lens stack.

The LEDs may comprise a light emitting surface. The light emitting surface(s) may emit light in the proximal-distal direction. The light emitting surface(s) may be positioned in abutment with the housing, where this is provided, or in abutment with one or more light guides.

If no light guide is present, the LED may be positioned adjacent a proximal end surface of the distal end wall, in which case the adhesive may not be present between a front surface of the LED and a proximal end of the light guide, or between a front surface of the LED and a proximal surface of the distal end wall. The light guide may be at least partly embedded in the adhesive. The light guide may include a light shield, in particular on a surface of the light guide facing the camera assembly. The light shield may be provided as a layer of colour or a material cladding with material having a low refraction index on said surface. In some embodiments the material may be air.

The light guide(s) may be in one piece with the distal end wall or they may be provided as separate parts that are attached to each other. The light guide may be manufactured or provided as a piece separate from the circumferential wall. Compared to solutions where a light guide is molded in one piece with a circumferential wall or a housing, this may make it possible to increase size or dimensions of the light guide and/or provide more freedom regarding positioning thereof since a molding tool may put limitations on e.g. possible dimensions of an airgap between the circumferential wall and the light guide.

Alternatively or additionally, the tip part assembly may comprise at least one steering section for steering a light guide, wherein the light guide may comprise light fiber(s). Such a steering section may be provided in one piece with or separately from, potentially attached to, the distal end wall.

In this specification, a proximal-distal direction may be defined as an axis extending along the parts of the insertion tube of the endoscope. Adhering to the definition of the terms distal and proximal, i.e. proximal being the end closest to the operator and distal being the end remote from the operator. The proximal-distal direction is not necessarily straight, for instance, if the insertion tube is bent, then the proximal-distal direction follows the curvature of the insertion tube. The proximal-distal direction may for instance be a centre line of the insertion tube.

Another embodiment of this disclosure concerns a method according to the first embodiment, wherein the method is also according to the second embodiment.

The steps a) to g) of the first embodiment may overlap or correspond to the steps a) to g) of the second embodiment.

This embodiment may alternatively be worded as:

A method of manufacture of a tip part assembly for an endoscope, the tip part assembly having a proximal end for being connected to other parts of the endoscope and a distal end positioned oppositely from the proximal end, the method comprising the steps of: a) providing a bendable bending section, the bending section including a proximal end and a distal end, b) providing a camera module and a circuit board, c) extruding a substantially tubular circumferential wall, the circumferential wall comprising a proximal end and a distal end, the circumferential wall proximal end being positioned oppositely from the circumferential wall distal end, d) providing a distal end wall, e) arranging the camera module so that the camera module is held by or attached to the distal end wall, f) subsequent to step e), manufacturing a housing of the tip part assembly by adjoining the distal end wall to the distal end of the circumferential wall so that the housing comprises the circumferential wall and the distal end wall, and so that the circumferential wall and the distal end wall enclose a spacing, at least a portion of the camera module being housed in the spacing, and g) subsequent to step f), adjoining the distal end of the bending section and the proximal end of the housing, so that the tip part assembly comprises the bending section, a camera assembly, and the housing, the camera assembly comprising the camera module and the circuit board in electrical connection with each other and being at least partly housed in the spacing, the distal end wall being positioned at the distal end of the tip part assembly.

This may provide a tip part assembly that is structurally stable and with high adhesive compatibility.

Another embodiment concerns a method according to the first or second embodiment, wherein step d) of the first or second embodiment comprises extruding the circumferential wall part and, subsequently, cutting a piece off of the circumferential wall part so that the piece constitutes the circumferential wall.

The piece constituting the circumferential wall may also be separated from the circumferential wall part in other ways than cutting. The circumferential wall part may be a circumferential wall workpiece or a circumferential wall blank.

This may reduce costs of manufacturing the tip part assembly.

The methods according to this disclosure may further comprise the steps of:
providing a working channel of the tip part assembly; and
arranging at least a portion of the working channel in the spacing.

The step of arranging at least a portion of the working channel in the spacing may be performed before or after the step of arranging the camera module/assembly and/or the step of adjoining the circumferential wall and the end wall. The step of arranging at least a portion of the working channel in the spacing may be performed before the step of adjoining the bending section and the housing.

This may provide a tip part assembly where tools and/or surgical instruments may be used, particularly where the tools and/or surgical instruments are inserted in the working channel. Liquids or other objects may also be extracted through the working channel.

The tip part assembly may further include a working channel extending through the spacing of the housing to a hole or an opening in the end wall. The working channel may extend into and/or through the distal end segment and/or the bending section. The working channel may extend proximally from the tip part assembly or a bending section thereof, potentially towards the proximal end of the endoscope. The working channel may allow liquid to be removed from a body cavity and/or allow insertion of surgical instruments or the like into the body cavity. The working channel may be provided as a channel extending from a proximal end of an endoscope to a distal end of the endoscope to guide a tool and/or to provide suction. A connector and/or a connecting portion may be provided at the proximal end of the endoscope to allow insertion of a tool into the working channel and/or to allow suction to be applied to the working channel. In some embodiments, the working channel comprises a built-in or integrated tool at or in the distal tip part assembly. Such a tool may be suitable for grabbing, taking, and/or holding elements in a part of a patient, in which the endoscope tip part is arranged during use.

The working channel may be tubular or substantially tubular and/or have a circumferentially extending, potentially cylindrical or circular cylindrical or substantially cylindrical or circular cylindrical, outer wall enclosing a working channel spacing. A material thickness of the tubular or substantially tubular wall may be less than or equal to 0.2 mm or less than or equal to s 0.15 mm. The working channel may have an inner diameter of 0.8 to 2 mm or 1 to 1.6 mm or 1 to 1.4 mm. A wall thickness of a circumferential wall of the working channel may be 0.1 to 0.5 mm.

Similar to as for a holding section for the camera module, the distal end wall may comprise a holding section for holding the working channel, the camera module being attached to and/or held in the holding section during positioning of the working channel. The holding section for the working channel may similarly include an opening or hole in the distal end wall, which opening may be circular and/or may be shaped to correspond to an outer surface of the working channel at a distal end of the working channel. The working channel distal end may be arranged in the opening, potentially by sliding the working channel distal end into the opening, potentially from a rear or proximal end of the opening and/or potentially in a longitudinal, distal direction. A holding bracket may extend from a distal end wall proximal surface to enclose at least part of the working channel, potentially may extend along one or more side surfaces of the working channel. A backstop may be provided e.g. on inner surfaces of the opening. Such a backstop may stop the working channel distal end from being slid through the opening and/or may allow for the working channel to be properly positioned at a desired location with respect to the distal end wall when being slid into the opening. In a final position of the working channel, a working channel distal opening may be positioned at a distance from a distal end wall distal or outer surface or may be plane with a distal end wall distal surface. An adhesive may be applied or injected into a slot between the working channel distal end and the opening. This adhesive may be applied together with an adhesive applied within the spacing and/or together with an adhesive applied in connection with the camera module as described above.

The adhesive may be applied along a periphery of the working channel. The adhesive may be applied from a proximal side of the opening(s), e.g. together with an adhesive applied in the spacing, or may be applied from a distal side or from a distal end of the tip part assembly or the of the openings. Either of the optional holding sections for the camera module and the working channel may be in one piece with the distal end wall, or the holding section(s) and the distal end wall may be provided in separate pieces attached to each other.

The working channel may alternatively be provided in one piece with the circumferential wall and may be extruded together with the circumferential wall, potentially as a multi-lumen tube or one tube provided within another tube. In this case, a working channel side surface can be attached to the circumferential wall at an inner side of the circumferential wall. In a cross-section, such an extruded multi-lumen tube may include two non-coaxial rings or circles touching or being connected to each other at one point or section of their peripheries.

The methods according to this disclosure may further comprise the step of:

filling a liquid adhesive into the spacing so that the camera assembly is at least partly embedded in the adhesive.

The step of filling the liquid adhesive into the spacing may be performed after the step of adjoining the circumferential wall and the distal end wall and, where the method comprises the steps of providing and arranging a working channel, after the steps of providing and arranging the working channel.

This may provide a tip part assembly with electrical insulation and structural stability and rigidity.

An outer maximum extent in a cross-sectional direction of the circumferential wall may be less than 3.3 mm.

Alternatively, an outer maximum extent in a cross-sectional direction of the tip part assembly may be less than 3.3 mm.

This outer maximum extent may be a maximum outer diameter of the circumferential wall and/or the housing and/or tip part assembly and may be a maximum cross sectional extent or a maximum diameter of the circumferential wall and/or the housing of the tip part assembly. The outer maximum extent may be less than 3.2, 3.1, 3.0. 2.9, 2.8, 2.7, 2.6 or 2.5 mm.

This may improve the comfort of the patient when the tip part assembly is inserted. It may also allow access to areas which were previously inaccessible or difficult to access.

A third aspect of this disclosure relates to a tip part assembly for an endoscope, the tip part assembly having a proximal end for being connected to other parts of the endoscope and a distal end positioned oppositely from the proximal end, the tip part assembly comprising: a bendable bending section, the bending section including a proximal end and a distal end, a camera assembly comprising a camera module, and a housing comprising an extruded substantially tubular circumferential wall, the circumferential wall comprising a proximal end and a distal end, the circumferential wall proximal end being positioned oppositely from the circumferential wall distal end, the housing further comprising a distal end wall positioned at the distal end of the tip part assembly, wherein the distal end of the circumferential wall is adjoined to the distal end wall so that the circumferential wall and the distal end wall enclose a spacing of the housing, wherein the distal end of the bending section is adjoined to the proximal end of the circumferential wall, and wherein the camera assembly is arranged to be at least partly housed in the spacing.

The tip part assembly for an endoscope according to the third aspect of this disclosure may have the same advantages as a tip part assembly according to the methods of the first and second aspects of this disclosure.

Any one of the above embodiments and the above individual and combined structural features of a tip part assembly manufactured according to the methods of this disclosure may also apply to the tip part assemblies according to this disclosure. For example, the circumferential wall may be circular cylindrical or substantially circular cylindrical or ring-shaped.

The tip part assembly may further comprise a working channel, wherein at least a portion of the working channel is arranged in the spacing.

At least the camera module may be attached or adhered to the housing by means of a hardened adhesive positioned within the spacing, the camera module being at least partly embedded in the adhesive, the adhesive being provided separately from the housing.

The adhesive may adhere the camera assembly and/or the circuit board and/or the camera module to the circumferential wall and/or to the distal end wall and/or to the housing.

An outer maximum extent in a cross-sectional direction of the housing may be less than 3.3 mm.

The distal end wall may further comprise at least one light guide and/or at least one steering section for steering a light guide.

The camera assembly may further comprise a circuit board in electrical connection with the camera module.

The tip part assembly may be manufactured according to the methods of the first aspect of this disclosure.

A fourth aspect of this disclosure relates to an endoscope comprising a tip part assembly manufactured according to the first or second aspect of this disclosure or a tip part assembly according to the third aspect of this disclosure.

The endoscope may comprise a control element. The control element may be configured to allow an operator to control a tip part assembly of the insertion tube by at least one steering wire. The control element may allow bending the tip part assembly in at least one direction, potentially in two directions, the two directions potentially being opposite. The control element may be accommodated in an operating handle. The control element may include a lever allowing an operator to control the control element. The lever may extend outwardly from the control element, potentially through an operating handle. The control element may be in the form of a roller or a roller disc.

The endoscope may comprise an operating handle. The operating handle may be suitable for allowing an operator to grip and to operate the endoscope, potentially with one hand. The operating handle may comprise a handle housing arranged at a proximal end of the insertion tube. The handle housing may accommodate the control element.

The insertion tube and/or a distal end thereof and/or the tip part assembly thereof may be suitable for insertion into a body cavity, potentially a kidney, through a body opening, potentially a urinary passage or a urethra. The body may be a natural and/or artificial body, potentially a human body. The insertion tube may extend from the operating handle towards a distal end of the endoscope.

Additionally or alternatively, the endoscope may form part of a system for visually inspecting otherwise difficult to access places such as human body cavities, the system further comprising a monitor. The endoscope may be connectable to the monitor, and the monitor may allow an operator to view an image captured by the camera assembly of the endoscope.

A person skilled in the art will appreciate that any one or more of the above aspects of this disclosure and embodiments thereof may be combined with any one or more of the other aspects of the disclosure and embodiments thereof.

BRIEF DESCRIPTION OF DRAWINGS

The tip part assemblies and methods will now be described in greater detail based on non-limiting exemplary embodiments and with reference to the drawings, on which.

DETAILED DESCRIPTION

Figure 1A:
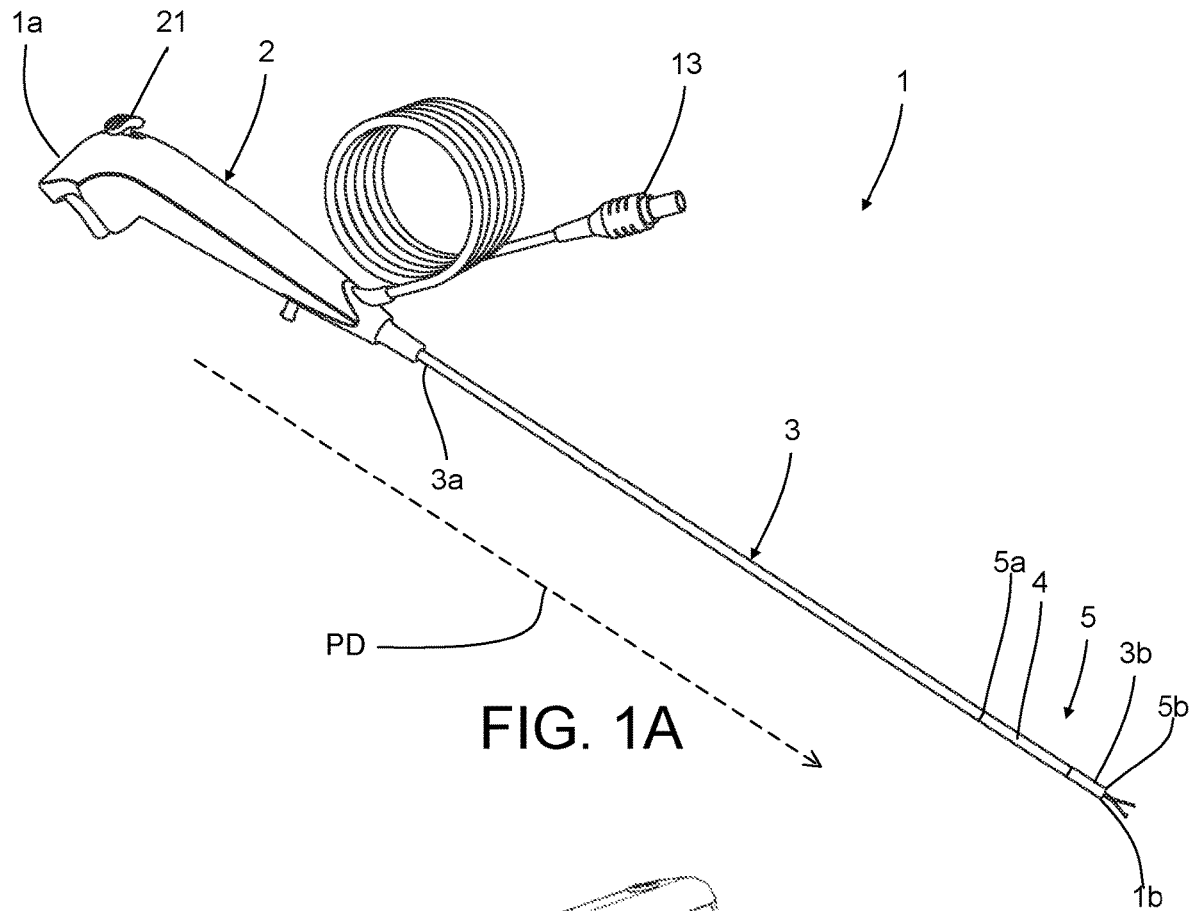
FIG. 1A shows a perspective view of an endoscope in which a tip part assembly according to the present disclosure is implemented.

Referring first to FIG. 1A, an endoscope 1 is shown. The endoscope is disposable, and not intended to be cleaned and reused. The endoscope 1 comprises an elongated insertion tube 3. At the proximal end 3*a* of the insertion tube 3 an operating handle 2 is arranged. The operating handle 2 has a control lever 21 for maneuvering a tip part assembly 5 at the distal end 3*b* of the insertion tube 3 by means of a steering wire and bending section 4. A camera assembly 6 is positioned in the tip part 5 and is configured to transmit an image signal through a monitor cable 12 of the endoscope 1 to a monitor 13.

The tip part assembly 5 has a proximal end 5*a* for being connected to other parts of the endoscope 1, and a distal end 5*b* positioned oppositely from the proximal end 5*a* forming the distal end 3*b* of the endoscope 1.

Figure 1B:
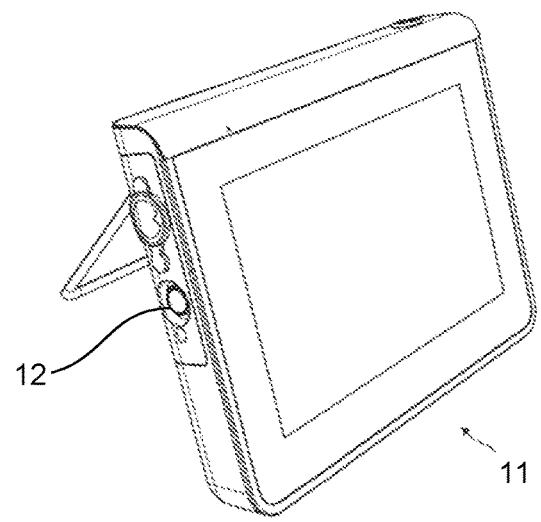
FIG. 1B shows a perspective view of a monitor to which the endoscope of FIG. 1A is connected.

In FIG. 1B, a monitor 11 is shown. The monitor 11 may allow an operator to view an image captured by the camera assembly 6 of the endoscope 1. The monitor 11 comprises a cable socket 12 to which a monitor cable 13 of the endoscope 1 can be connected to establish a signal communication between the camera assembly 6 of the endoscope 1 and the monitor 11.

The proximal-distal direction PD is an axis extending along the parts of the insertion tube 3 of the endoscope 1.

According to the method of the first embodiment disclosed herein, the tip part assembly 5 is manufactured by the steps of: a) providing a bendable bending section 4 which includes a proximal end 4*a* and a distal end 4*b*, b) providing a camera assembly 6 comprising a camera module 60 and a circuit board 70 in electrical connection with each other, c) providing a substantially tubular circumferential wall 8*g*, the circumferential wall 8*g* comprising a proximal end 8*a* and a distal end 8*b*, the circumferential wall proximal end 8*a* being positioned oppositely from the circumferential wall distal end 8*b*, d) providing a distal end wall 8*e*, 8*e*', 8*e*", 8*e*'", e) arranging the camera module 60 so that the camera module 60 is held by or attached to the distal end wall 8*e*, 8*e*', 8*e*", 8*e*'", f) subsequent to step e), manufacturing a housing 8, 8', 8" of the tip part assembly 4 by adjoining the distal end wall 8*e*, 8*e*', 8*e*", 8*e*'" to the distal end 8*b* of the circumferential wall 8*g* so that the housing 8, 8', 8" comprises the circumferential wall 8*g* and the distal end wall 8*e*, 8*e*', 8*e*", 8*e*'" and so that the circumferential wall 8*g* and the distal end wall 8*e*, 8*e*', 8*e*", 8*e*'" enclose a spacing, at least a portion of the camera module 60 being housed in the spacing, and g) subsequent to step f), adjoining the distal end 4*b* of the bending section 4 and the proximal end 8*a* of the housing 8, 8', 8", so that the tip part assembly 5 comprises the bending section 4, the camera assembly 60, and the housing 8, 8', 8", the camera assembly 60 being at least partly housed in the spacing, the distal end wall 8*e*, 8*e*', 8*e*", 8*e*'" being positioned at the distal end 5*b* of the tip part assembly 5.

Alternatively, the tip part assembly 5 may be manufactured according to the method of the second embodiment which shares steps a)-b) with the first embodiment and comprises the following steps of: c) extruding a substantially tubular circumferential wall 8*g*, the circumferential wall 8*g* comprising a proximal end 8*a* and a distal end 8*b*, the circumferential wall proximal end 8*a* being positioned oppositely from the circumferential wall distal end 8*b*, d) providing a distal end wall 8*e*, 8*e*', 8*e*", 8*e*'", e) arranging the camera module 60 so that the camera module 60 is held by or attached to the distal end wall 8*e*, 8*e*', 8*e*", 8*e*'", f) manufacturing a housing 8, 8', 8" of the tip part assembly 5 by adjoining the distal end wall 8*e*, 8*e*', 8*e*", 8*e*'" to the distal end 8*b* of the circumferential wall 8*g* so that the housing 8, 8', 8" comprises the circumferential wall 8*g* and the distal end wall 8*e*, 8*e*', 8*e*", 8*e*'" and so that the circumferential wall 8*g* and the distal end wall 8*e*, 8*e*', 8*e*", 8*e*'" enclose a spacing, and g) adjoining the distal end 4*b* of the bending section 4 and the proximal end 8*a* of the housing 8, 8', 8", so that the tip part assembly 5 comprises the bending section 4, the camera assembly 6, and the housing 8, 8', 8", the camera assembly 6 being at least partly housed in the spacing, the distal end wall 8*e*, 8*e*', 8*e*", 8*e*'" being positioned at the distal end 5*b* of the tip part assembly 5.

Another embodiment of this disclosure concerns a method according to the first embodiment, wherein the method is also according to second embodiment. The steps a) to g) of the first embodiment may overlap or correspond to the steps a) to g) of the second embodiment.

Figure 2:
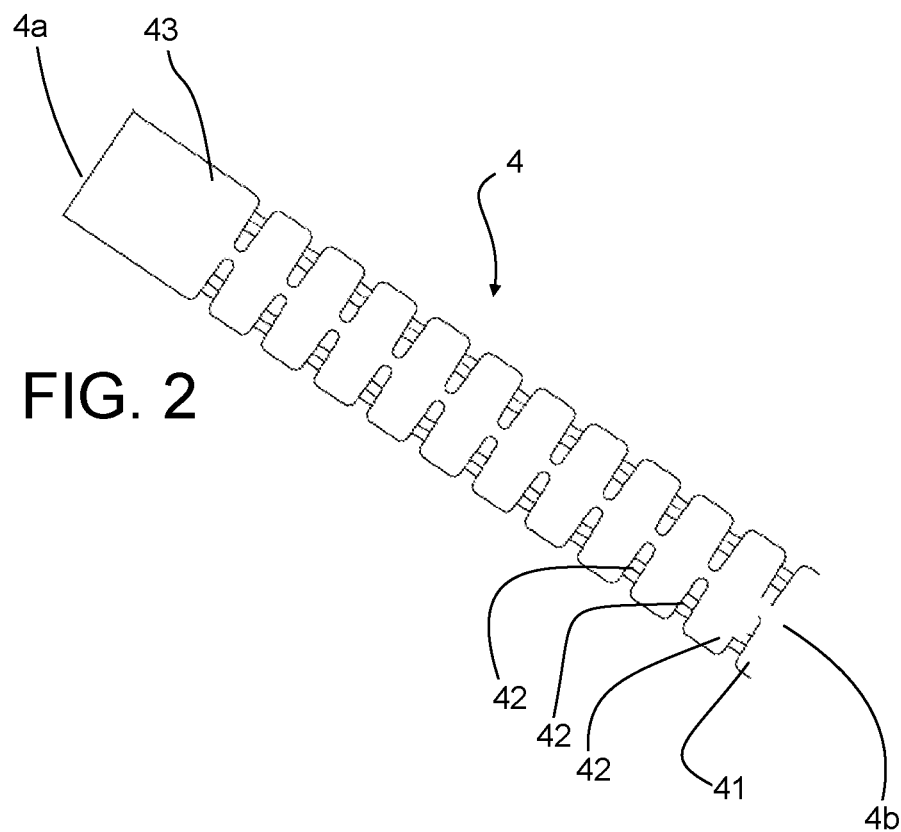
FIG. 2 shows a side view of a bending section of the endoscope of FIG. 1A and FIG. 1B.

Turning to FIG. 2, a plane view of the bending section 4 is provided. The bending section 4 allows the tip part assembly 5 to bend relative to the insertion tube 3, so as to allow an operator to manipulate the tip part assembly 5 while inserted into a body cavity of a patient. The bending section 4 is molded in one piece, but may alternatively be constituted by a plurality of molded pieces. The bending section 4 comprises a number of hingedly connected segments including a distal end segment 41, a proximal segment 43, and a plurality of intermediate segments 42 positioned between the distal end segment 41 and the proximal segment 43. The distal end segment 41 is adapted for being connected and/or attached to a housing 8, 8', 8" of a tip part assembly, such as the housing 8, 8', 8", of FIGS. 4A-4F at a proximal end 8*a* of the housing 8, 8', 8". An adhesive is separately applied to adjoin the bending section end segment 41 to the housing 8, 8', 8".

Figure 3:
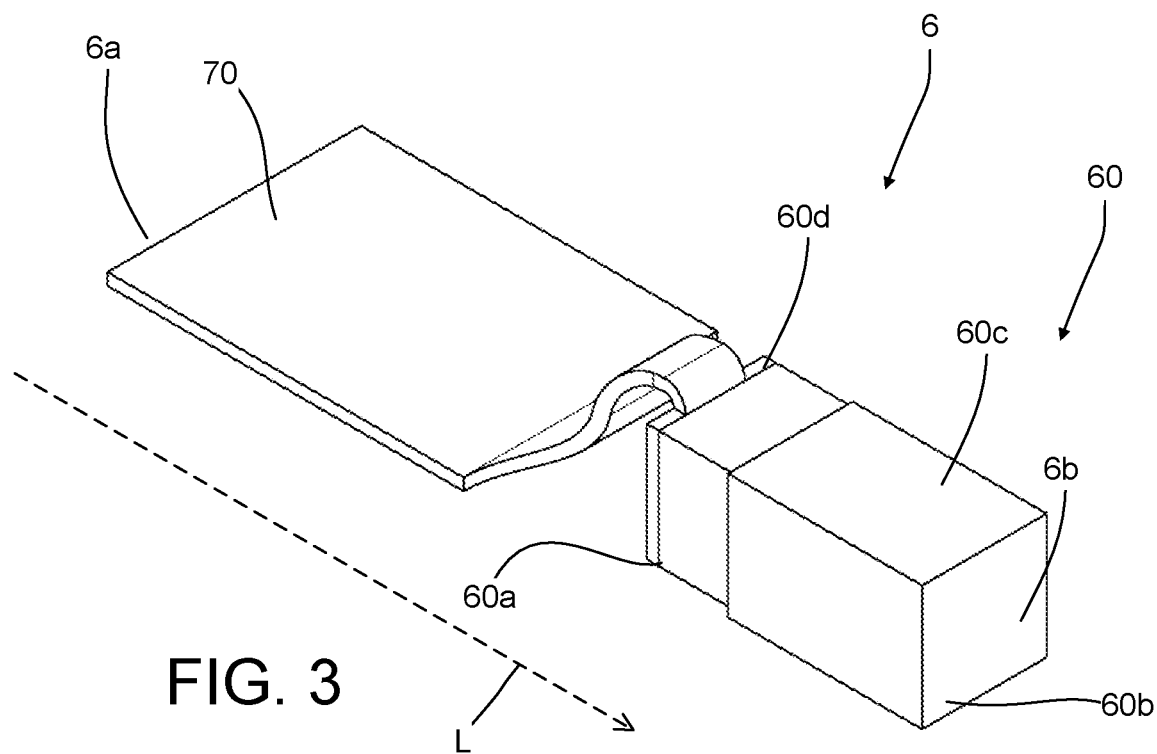
FIG. 3 shows a perspective view of a camera assembly of a tip part assembly of FIGS. 1A and 1B.

FIG. 3 shows a perspective view of the camera assembly 6 which is a sub-assembly of the tip part assembly 5 and comprises camera module 60 a circuit board 70, and a substantially box-shaped camera module housing 60c. Inside the camera module housing 60c an image sensor (not shown) and a stacked lens stack (not shown) is arranged. The lens stack is positioned distally of the image sensor and includes a proximal lens and a distal lens. The camera module 60 further comprises a lens barrel (not shown) extending in the longitudinal direction, and which holds and encases the lens stack. The camera module 60 extends in the longitudinal direction L.

The circuit board 70 is electrically connected to the camera module 60 through a proximal connection surface 60d at a proximal end 60d of the camera module 60. The circuit board 70 is a printed circuit board (PCB). Alternatively, the circuit board 70 could be a flexible printed circuit (FPC)

Turning to FIGS. 4A-4F, different embodiments of the tip part assembly are shown. The housing 8, 8', 8" is manufactured by adjoining a circumferential wall 8g and a distal end wall 8e, 8e', 8e", 8e'". The housing 8, 8', 8" provides electrical insulation and water tightness around the camera assembly 6 and electrical connections within the housing 8, 8', 8". The housing 8, 8', 8" also ensures that a minimum insulation thickness is present on all outer surfaces of the tip part assembly 5.

The circumferential wall 8g is cylindrical and has constant circular cross-sectional profile. The wall 8g is an outer wall and defines an outer surface of the tip part assembly 5 for facing the environment. No parts of the tip part assembly 5 are positioned outside an outer circumference of the circumferential wall 8g. Manufacture of the circumferential wall 8g includes extrusion of the circumferential wall 8g through a die which has a ring-shaped cross section and cutting the extruded circumferential wall 8g to length.

The length in a longitudinal direction of the circumferential wall 8g is 10 mm and has a wall thickness of 0.15 mm. The outer maximum extent in a cross-sectional direction, which is the outer maximum diameter of the circumferential wall 8g, is less than 3.3 mm.

In some embodiments step d) of the first or second embodiment comprises extruding the circumferential wall part and, subsequently, cutting a piece off of the circumferential wall part so that the piece constitutes the circumferential wall 8g. The circumferential wall part is a circumferential wall blank.

The circumferential wall 8g extends to cover a bending section distal end segment 41 and is bendable, allowing the circumferential wall 8g to follow bending of the bending section 4.

The circumferential wall 8g is provided separately from the distal end wall 8e, 8e', 8e", 8e'" before it is adjoined with the distal end wall 8e, 8e', 8e".

In step e) of the methods of this disclosure, the circumferential wall 8g is positioned such that the it does not enclose the camera module 60, the camera assembly 6, or any other components of the tip part assembly 5, which allows for more space around the camera module 60 and distal end wall 8e, 8e', 8e", 8e'" during step e).

The distal end wall 8e, 8e', 8e", 8e'" is provided in step d) as a part separate from the circumferential wall 8g, i.e. not in one piece with the circumferential wall 8g and is molded.

The electrical connection between the circuit board 70 and the camera module 60 is established in step b). Alternatively, it may be established during or after any one of steps e), f), and g).

As seen in FIGS. 4A-4F, the distal end wall 8e, 8e', 8e", is positioned at the distal end 5a of the assembled tip part assembly 5. The distal end wall 8e, 8e', 8e", 8e'" comprises a holding section 8h for holding the camera module 60 as seen in FIGS. 5A-6B. In step e) of the methods of this disclosure, the camera module 60 is attached and held in the holding section 8h. The holding section 8h includes an opening 8i which is shaped to correspond to the outer surface of the camera module 60 at the distal end 60b of the camera module 60, in the distal end wall 8e, 8e', 8e", 8e'". The camera module distal end 60b is arranged in the opening 8i in step e), by sliding the camera module distal end 60b into the opening 8i, from a proximal end of the opening 8i in a distal direction. The camera module 60 may be held in the camera holding aperture/section by friction, initially, until the adhesive secures the camera module 60 in the spacing. The camera assembly may comprise a front lens/window attached to the barrel that is exposed, through the camera holding aperture/section, to the body cavities, best shown in FIGS. 4E, 4F, and 5A-C.

Figure 4A:
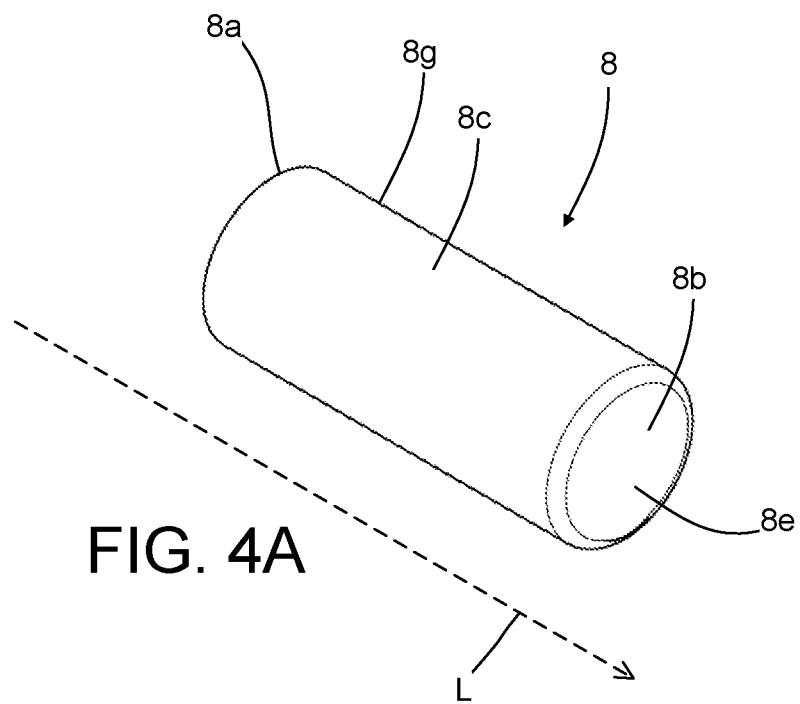
FIG. 4A shows a perspective view of a first embodiment of a tip part assembly of FIGS. 1A and 1B.
Figure 4B:
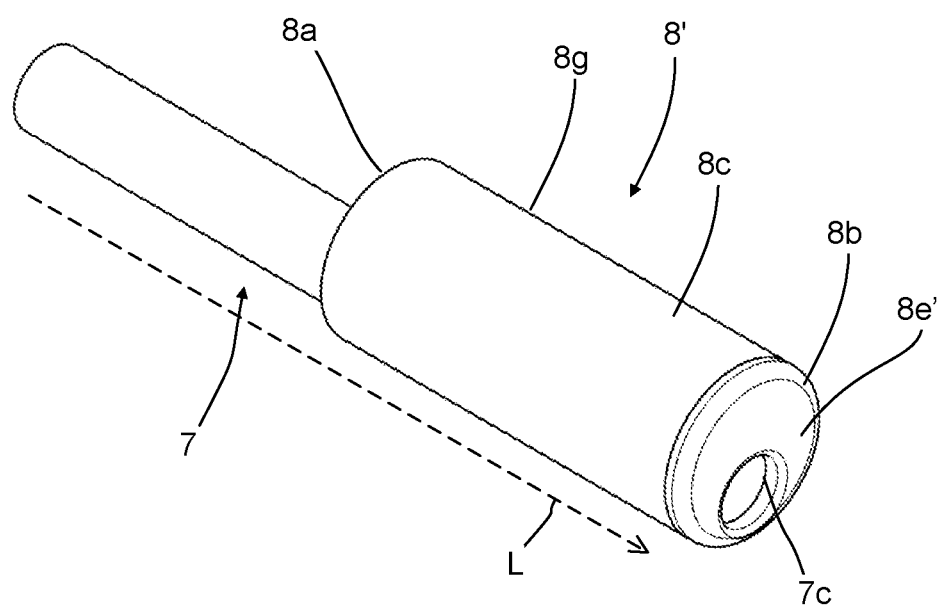
FIG. 4B shows a perspective view of a second embodiment of a tip part assembly of FIGS. 1A and 1B.
Figure 4C:
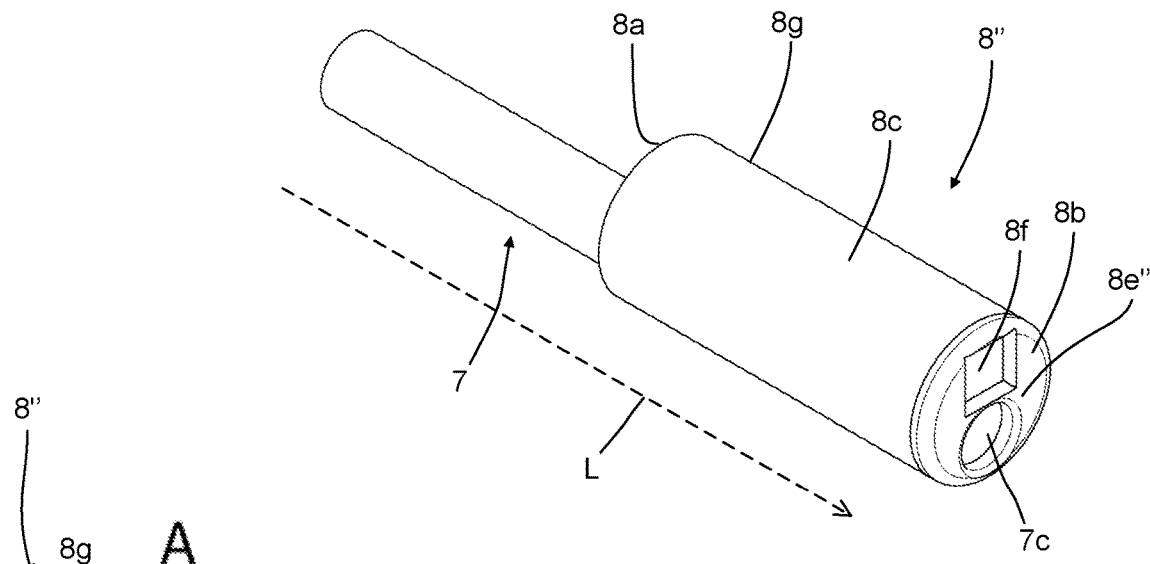
FIG. 4C shows a perspective view of a third embodiment of a tip part assembly of FIGS. 1A and 1B.
Figure 4D:
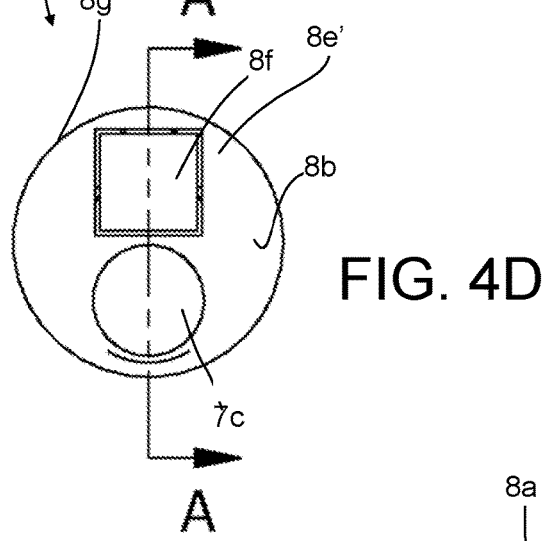
FIG. 4D shows a view onto the distal end of the tip part assembly of FIG. 4C.
Figure 4E:
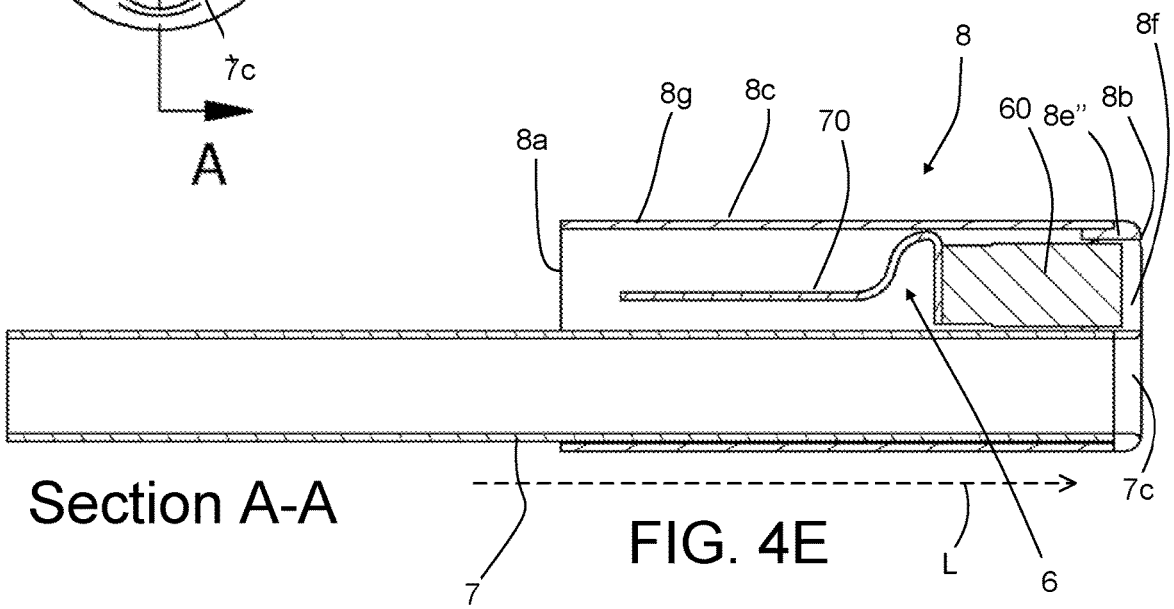
FIG. 4E shows a section view A-A of the tip part assembly of FIG. 4C.

Alternatively, the distal front surface of the camera module 60 is provided proximally of the distal end wall 8e, 8e', 8e", 8e'" adjacent to distal end wall proximal surface such as in the embodiment shown in FIG. 4A. Here the distal end wall 8e does not include a camera module opening 8i, but rather extends in front of the camera module distal end surface. In this case, the distal end wall 8e is transparent to allow light to shine through the distal end wall 8e into the camera module 60. This also applies to the distal end wall 8e' in FIG. 4B.

In a final position of the camera module 60, a camera module front surface, which is a distal lens front surface (not shown), is plane with a distal end wall distal surface. Alternatively, the distal lens front surface may be positioned at a distance from the distal end wall distal surface in the final position of the camera module 60. To aid fixation of the camera module 60 relative to the distal end wall 8e, 8e', 8e", 8e'" an adhesive is applied into a slot between the camera module distal end 60b and the opening 8i. This adhesive is applied together with an adhesive applied within the spacing.

The circumferential wall 8g and the distal end wall 8e, 8e', 8e", 8e'" are of an electrically insulating and transparent material. The circumferential wall 8g consists of acrylic and the distal end wall 8e, 8e', 8e", 8e'" consists of polycarbonate. They may alternatively consist of the same material.

Adjoining of circumferential wall 8g and the distal end wall 8e, 8e', 8e", 8e'" is performed by means of an adhesive, which is be applied between an inner surface of the circumferential wall 8g and outer surface of the distal end wall 8e, 8e', 8e", 8e'" facing the inner surface of the circumferential wall 8g. The bending section 4 and the housing 8, 8', 8" are adjoined by applying an adhesive to the distal end of the bending section 4b and the proximal end of the housing 8a. The adhesive used to adjoin the distal end of the bending section 4a and the proximal end of the housing 8a is the same type of adhesive as the one used to adjoin the distal end wall 8e, 8e', 8e", 8e'" and the circumferential wall 8g.

Figure 4F:
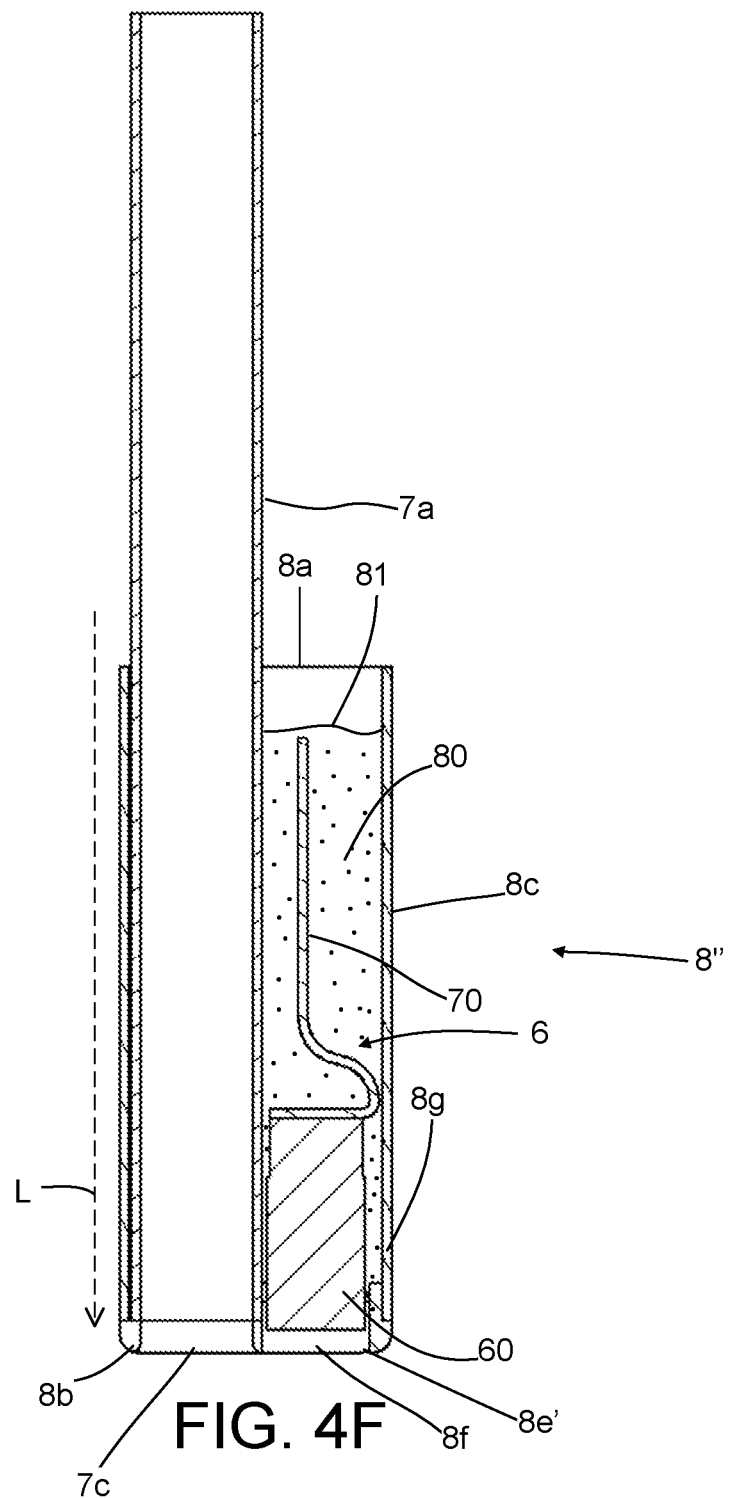
FIG. 4F shows a section view of the tip part assembly of FIG. 4C with an adhesive filled into the spacing

To secure the camera assembly 6 and the working channel 7 in the housing 8, 8', 8", an adhesive 80 is filled into the spacing of the housing 8, 8', 8" so that the camera assembly 6 is embedded in the adhesive 80 as seen in FIG. 4F. The adhesive 80 is then caused to harden, whereby the adhesive 80 attaches the housing 8, 8', 8" and the camera assembly 6 to each other. Electronic wires (not shown) for connecting the circuit board 70 to other parts of the endoscope are also partly embedded in the adhesive 80. This is advantageous since wires or cables may be pulled during operation of the endoscope, pulling also in the circuit board 70, especially during bending of a bending section 4 of the tip part assembly 5. The adhesive is a liquid adhesive 80 with electrically insulating properties and is of a low dynamic viscosity below or equal to 200 cP (centipoise, which is equal to mPa's). This helps ensure that the adhesive 80 reaches substantially all corners of a free volume of the spacing.

The adhesive 80 is a silicone adhesive and is poured into the spacing through an open proximal end of the housing 8, 8', 8". To ensure a correct amount of adhesive 80 is filled into the spacing in the housing 8, 8', 8", an upper level 81 of the adhesive 80 is measured during filling. Alternatively, a predefined amount of adhesive may be measured off and poured into the spacing in the housing 8, 8', 8". The adhesive 80 acts as a potting material and provides the tip part assembly 6 with greater robustness, mechanical stability, and rigidity. To ensure the adhesive 80 is hardened and cured correctly it is heat cured after being filled into the spacing in the housing 8, 8', 8".

In some embodiments, the methods according to this disclosure may further comprise the steps of: providing a working channel 7 of the tip part assembly 5; and arranging at least a portion of the working channel 7 in the spacing.

The step of arranging at least a portion of the working channel 7 in the spacing is performed before the step of arranging the camera module/assembly and/or the step of adjoining the circumferential wall 8g and the distal end wall 8e, 8e', 8e", 8e'''.

As seen in FIGS. 4B-4F the second and third embodiment include a working channel 7 extending through the spacing of the housing 8', 8" to an opening 7c in the distal end wall 8e', 8e". The working channel 7 further extends into the distal end segment 41 and the bending section 4 and proximally through the insertion tube 3. The working channel 7 allows liquid to be removed from a body cavity and insertion of surgical instruments or the like into the body cavity. A connecting portion (not shown) is provided at the proximal end of the endoscope 1a to allow insertion of a tool into the working channel 7 and to allow suction to be applied to the working channel 7. In some embodiments, the working channel 7 comprises a built-in or integrated tool at or in the distal tip part assembly 5. Such a tool may be suitable for grabbing, taking, and/or holding elements in a part of a patient, in which the endoscope tip part is arranged during use.

As shown, the working channel 7 is tubular and has a circumferentially extending tubular circular cylindrical outer wall enclosing a working channel spacing. The material thickness of the tubular wall is less than 0.15 mm. The working channel 7 has an inner diameter of 1.2 mm. Non-circular outer walls are also permissible, e.g. oval.

Returning to FIGS. 5A and 5B, similar to a holding section 8h for the camera module 60, the distal end wall 8e, 8e', 8e", 8e''' comprises a holding section 8j for holding the working channel 7, the camera module 60 being held in the holding section 8h during positioning of the working channel 7. The holding section 8j for the working channel 7 similarly includes an opening 7c in the distal end wall 8e, 8e', 8e", 8e''', which opening 7c is shaped to correspond to an outer surface of the working channel 7c at a distal end of the working channel 7c. The working channel distal end is arranged in the opening 7c by sliding the working channel distal end into the opening 7c, from a rear or proximal end of the opening 7c in the longitudinal, distal direction L. The working channel holding section 8j may comprise a holding bracket and a backstop as disclosed for the camera module holding section 8h. Like the camera module 60, the working channel 7 is attached in the holding section 8j by an adhesive. This adhesive is applied together with the adhesive applied in connection with the camera module 60 as disclosed above. The adhesive is applied along a periphery of the working channel 7c.

Figure 5A:
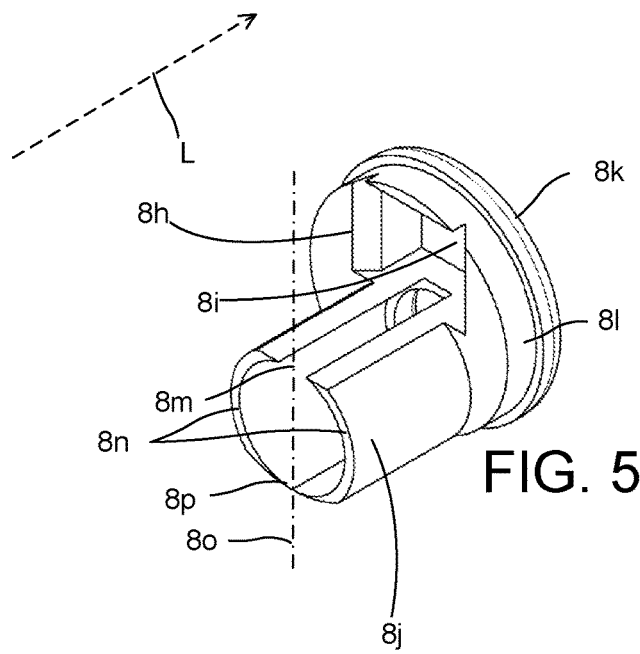
FIG. 5A shows a first embodiment of a distal end wall.
Figure 5C:
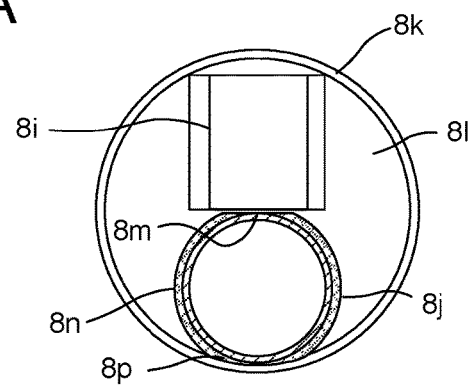
FIG. 5C is a proximal view of the distal end wall of FIGS. 5A and 5C holding the working channel/tube.
Figure 5B:
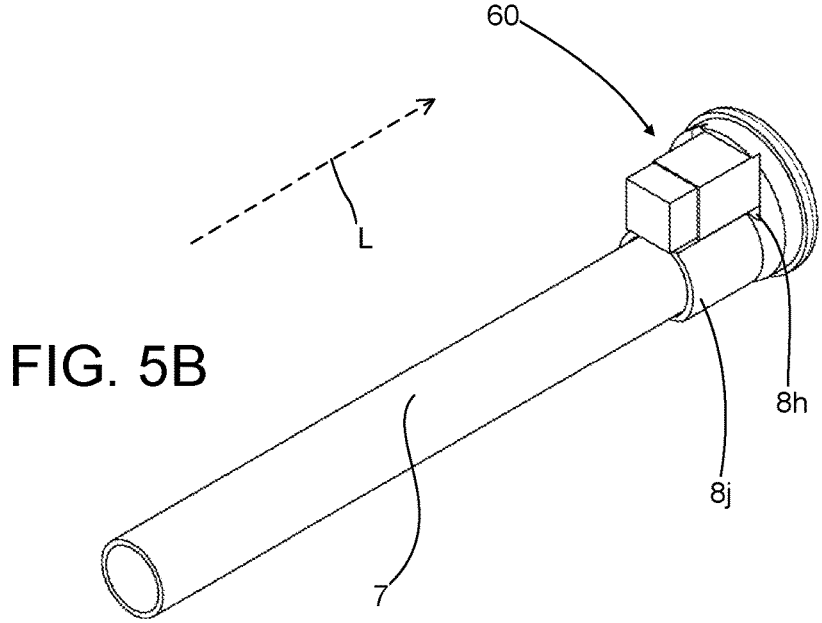
FIG. 5B is a perspective view of the distal end wall of FIG. 5A holding a camera module and a working channel.

As best seen in FIGS. 5B and 5C, the distal end wall 8e''' comprises a distal wall section 8k and an internal section 8l extending proximally from the distal wall section, wherein the distal wall section and the internal section comprise a camera module opening 8i sized and shaped to match a size and shape of the camera module, and wherein at least a portion of the camera module is received by the camera module opening 8i. The internal section 8l fits within and is affixed to the internal surface of the circumferential wall during assembly. LEDs 9 and light guides 50 (shown in FIGS. 6A and 6B) may be affixed to the internal section 8l. The light guides 50 may also be molded in one piece with the distal end wall 8e'''. The LEDs 9 may be electrically connected to the circuit board 70 to receive power therefrom, in any known manner. The distal end wall 8e''' may be transparent to allow light emitted from the LEDs 9 to illuminate the field of view of the camera module.

The holding section 8j comprises a longitudinal wall extending proximally from the distal end wall 8e, 8e', 8e", 8e'''. As shown in FIGS. 5B and 5C, the longitudinal wall may be cylindrical and comprises a cut-out 8m adjacent, when the distal tip is assembled, the camera module 60. At a location opposite the cut-out 8m, denoted by numeral 8p, the wall thickness of the longitudinal wall is reduced. The camera module opening and the working channel/tube holding section define a vertical extent 80 of the housing. The working tube holding section comprises opposite wall sections 8n parallel to the vertical extent which are thicker than a wall section 8p traversing or adjacent the vertical extent. The design of the cut-out and thinner wall thickness reduce the cross-section of the tip part assembly and enable manufacture of an endoscope with a smaller insertion section. The working tube holding section can additionally include a longitudinal cut-out in addition to or in lieu of thin wall section 8p. The upper and lower longitudinal cut-outs are sized and shaped to reduce a distance between the camera module and the lower portion of the circumferential wall of the housing (e.g. a distance that includes the diameter of the working channel/tube holding section) by minimizing the distance between the camera module and the working channel/tube holding section and also between the working channel/tube holding section and the circumferential wall, thus enabling production of an endoscope with a very small cross-section. In addition to the cut-outs, the surfaces of the longitudinal wall forming the working channel/tube holding section adjacent at least the camera module are flattened transversely to the longitudinal extent, as shown in FIG. 5C, to further reduce the distance.

Figure 6A:
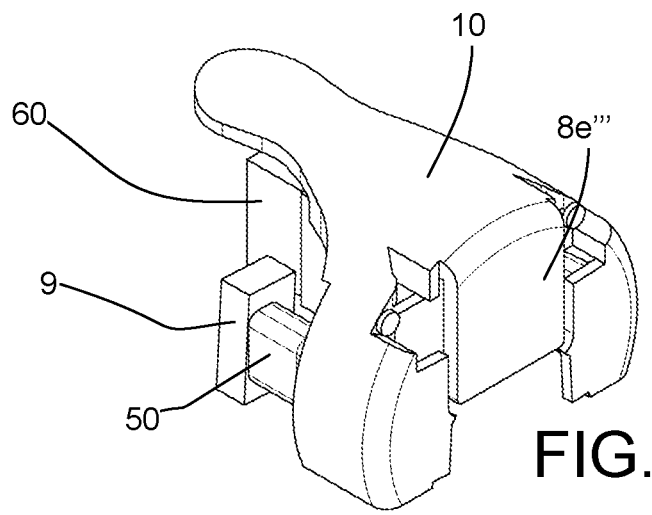
FIG. 6A shows a perspective view of a section of a distal end wall.
Figure 6B:
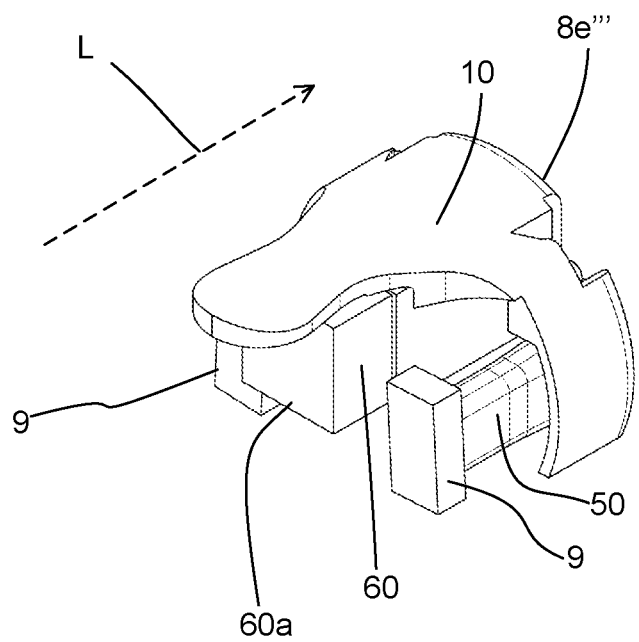
FIG. 6B shows a different perspective view of the distal end wall in FIG. 6A.

Turning to FIGS. 6A and 6B, the tip part assembly 5 further includes two LEDs 9 for illuminating a target of the endoscope 2 as seen in FIGS. 6A and 6B. The LEDs 9 are positioned at the proximal end of light guides 50 and are substantially embedded in the adhesive 80 with the exception of a light emitting surface. The tip part assembly 5 also includes two light guides 50, of which one is shown in FIG. 6A, for guiding light from a respective LED 9 to a distal end surface of the end wall 8e, 8e', 8e", 8e'''. In FIGS. 6A and 6B the light guides 50 are provided as separate pieces from the distal end wall 8e''' and then attached to thereto. The light guides 50 are also separate from the circumferential wall 8g. It is also possible to mold the light guides 50 in one piece with the distal end wall 8e, 8e', 8e", 8e'''. As shown in FIGS. 6A and 6B, the housing of the tip part assembly is formed by adjoining the distal end wall 8e''' to the distal end of the circumferential wall so that the housing comprises the circumferential wall and the distal end wall. In this case a transparent portion 10 of the housing, formed with the front wall, extends proximally from the front wall 8e'''.

The tip part assembly 5 also comprises a steering section (not shown) for steering the light guides 50 that comprise light fibers. The steering section may be provided separately from the distal end wall 8e'''.

The following additional examples expand and further exemplify the features described above:

(1) A method of manufacture of a tip part assembly for an endoscope, the tip part assembly having a proximal end for being connected to other parts of the endoscope and a distal end positioned oppositely from the proximal end, the method comprising the steps of: providing a bendable bending section, the bending section including a proximal end and a distal end, providing a camera assembly comprising a camera module, providing a substantially tubular circumferential wall, the circumferential wall comprising a proximal end and a distal end, the circumferential wall proximal end being positioned oppositely from the circumferential wall distal end, providing a distal end wall, arranging the camera module so that the camera module is held by or attached to the distal end wall, manufacturing a housing of the tip part assembly by adjoining the distal end wall to the distal end of the circumferential wall so that the housing comprises the circumferential wall and the distal end wall, and so that the circumferential wall and the distal end wall enclose a spacing, at least a portion of the camera module being housed in the spacing, and, adjoining the distal end of the bending section and the proximal end of the housing, so that the tip part assembly comprises the bending section, the camera assembly, and the housing, the camera assembly being at least partly housed in the spacing, the distal end wall being positioned at the distal end of the tip part assembly.

(2) A method of manufacture of a tip part assembly for an endoscope, the tip part assembly having a proximal end for being connected to other parts of the endoscope and a distal end positioned oppositely from the proximal end, the method comprising the steps of: providing a bendable bending section, the bending section including a proximal end and a distal end, providing a camera assembly comprising a camera module, extruding a substantially tubular circumferential wall, the circumferential wall comprising a proximal end and a distal end, the circumferential wall proximal end being positioned oppositely from the circumferential wall distal end, providing a distal end wall, arranging the camera module so that the camera module is held by or attached to the distal end wall, manufacturing a housing of the tip part assembly by adjoining the distal end wall to the distal end of the circumferential wall so that the housing comprises the circumferential wall and the distal end wall, and so that the circumferential wall and the distal end wall enclose a spacing, and adjoining the distal end of the bending section and the proximal end of the housing, so that the tip part assembly comprises the bending section, the camera assembly, and the housing, the camera assembly being at least partly housed in the spacing, the distal end wall being positioned at the distal end of the tip part assembly.

(3) A method according to (1), wherein the method is also according to (2).

(4) A method according to (1) or (2), wherein providing a distal end wall comprises extruding the circumferential wall part and, subsequently, cutting a piece off of the circumferential wall part so that the piece constitutes the circumferential wall.

(5) A method according to any one of (1)-(4), further comprising the steps of:
providing a working channel of the tip part assembly; and arranging at least a portion of the working channel in the spacing.

(6) A method according to any one of (1)-(5), further comprising the step of:
filling a liquid adhesive into the spacing so that the camera assembly is at least partly embedded in the adhesive.

(7) A method according to any one of (1)-(6), wherein an outer maximum extent in a cross-sectional direction of the circumferential wall is less than 3.3 mm.

(8) A method according to any one of (1)-(7), wherein the tip part assembly further comprises at least one light guide.

(9) A tip part assembly for an endoscope, the tip part assembly having a proximal end for being connected to other parts of the endoscope and a distal end positioned oppositely from the proximal end, the tip part assembly comprising: a bendable bending section, the bending section including a proximal end and a distal end, a camera assembly comprising a camera module, and a housing comprising an extruded substantially tubular circumferential wall, the circumferential wall comprising a proximal end and a distal end, the circumferential wall proximal end being positioned oppositely from the circumferential wall distal end, the housing further comprising a distal end wall positioned at the distal end of the tip part assembly, wherein the distal end of the circumferential wall is adjoined to the distal end wall so that the circumferential wall and the distal end wall enclose a spacing of the housing, wherein the distal end of the bending section is adjoined to the proximal end of the circumferential wall, and wherein the camera assembly is arranged to be at least partly housed in the spacing.

(10) A tip part assembly according to (9), further comprising a working channel, wherein at least a portion of the working channel is arranged in the spacing.

(11) A tip part assembly according to (9) or (10), wherein at least the camera module is attached or adhered to the housing by means of a hardened adhesive positioned within the spacing, the camera module being at least partly embedded in the adhesive, the adhesive being provided separately from the housing.

(12) A tip part assembly according to any one of (9) to (11), wherein an outer maximum extent in a cross-sectional direction of the housing is less than 3.3 mm.

(13) A tip part assembly according to any one of (9) to (12), wherein the distal end wall further comprises at least one light guide and/or at least one steering section for steering a light guide.

(14) A tip part assembly for an endoscope, wherein the tip part assembly is manufactured according to the method of any one of (1) to (8).

(15) An endoscope comprising a tip part assembly manufactured according to any one of (1) to (8) or a tip part assembly according to any one of (9) to (14).

LIST OF REFERENCES

The following is a list of reference numerals used throughout this specification.
1 endoscope
11 monitor
12 cable socket
13 monitor cable
2 handle
21 control lever
3 insertion tube
3a proximal end
3b distal end
4 bending section
4a bending section proximal end
4b bending section distal end
41 distal end segment
42 intermediate segment
43 proximal segment
tip part assembly
5a tip part assembly proximal end
5b tip part assembly distal end
50 light guide
6 camera assembly
6a camera assembly proximal end
6b camera assembly distal end
60 camera module
60a camera module proximal end
60b camera module distal end
60c camera module housing
60d camera module connecting surface
7 working channel
7c working channel hole or opening
70 circuit board
8 housing
8a housing proximal end
8b housing distal end
8c outer surface
8e distal end wall
8e' distal end wall
8e" distal end wall
8e'" distal end wall
8f window
8g circumferential wall
8h camera module holding section
8i holding section opening
8j working channel holding section
80 liquid adhesive
81 adhesive level
9 light-emitting diode (LED)
L longitudinal direction
PD proximal-distal direction

The invention claimed is:

1. A method to manufacture an endoscope, the method comprising:
providing a bending section including a proximal end and a distal end;
providing a camera assembly comprising a camera module;
providing a circumferential wall, the circumferential wall being substantially tubular and comprising a proximal end and a distal end opposite from the proximal end, the circumferential wall comprising an inner surface and an outer surface opposite the inner surface;
providing a distal end wall comprising a distal end wall outer surface, including a distal end wall distal surface, and further comprising a distal end wall proximal surface opposite the distal end wall distal surface, the distal wall further comprising a working tube holding section affixed to an extending proximally from a distal wall section, distal end wall distal surface exposed to the external environment;
arranging the camera module and the distal end wall so that the camera module is held by or attached to the distal end wall;
subsequent to arranging the camera module and the distal end wall, adjoining the distal end wall to the distal end of the circumferential wall to form a housing having a spacing therein with at least a portion of the camera module positioned in the spacing; and
adjoining the distal end of the bending section and the proximal end of the circumferential wall,
wherein a camera module opening and the working tube holding section define a vertical extent of the housing, and
wherein the working tube holding section comprises opposite wall sections parallel to the vertical extent and a wall section between the opposite wall sections of the working tube holding section and traversing the vertical extent, the opposite wall sections and the wall section between them extending proximally from the distal end wall, and the opposite wall sections being thicker than the wall section between them.

2. The method of claim 1, further comprising extruding the circumferential wall before providing the circumferential wall.

3. The method of claim 2, wherein extruding the circumferential wall comprises extruding a tube and cutting the circumferential wall from the tube.

4. The method of claim 1, further comprising inserting a distal end of a working tube into the working tube holding section, the working tube extending from the working tube holding section through the bending section.

5. The method of claim 1, wherein the distal end wall comprises a single-piece part including the distal wall section and an internal section extending proximally from the distal wall section, wherein the distal wall section and the internal section comprise the camera module opening sized and shaped to match a size and shape of the camera module, and wherein at least a portion of the camera module is received by the camera module opening.

6. The method of claim 1, further comprising mounting a working tube over the working tube holding section prior to adjoining the distal end wall to the distal end of the circumferential wall.

7. The method of claim 1, wherein the working tube holding section comprises a longitudinal cut-out traversing the vertical extent and located adjacent the camera module opening.

8. The method of claim 1, further comprising positioning at least a portion of a working channel in the spacing of the housing.

9. The method of claim 1, further comprising filling the spacing at least partially with a liquid adhesive to at least partly embed the camera module.

10. The method of claim 1, wherein an outer maximum extent in a cross-sectional direction of the circumferential wall is less than 3.3 mm.

11. The method of claim 1, wherein the endoscope further comprises at least one light guide.

12. The method of claim 1, wherein adjoining the distal end wall to the distal end of the circumferential wall comprises applying an adhesive between the inner surface of the circumferential wall and the outer surface of the distal end wall.

13. The method of claim 1, further comprising filling at least a portion of the spacing of the housing with an adhesive to at least partially embed the camera assembly in the adhesive.

14. The method of claim 13, wherein filling the at least the portion of the spacing comprises inserting a predetermined amount of the adhesive.

* * * * *